United States Patent
Arnold et al.

(10) Patent No.: US 6,389,885 B1
(45) Date of Patent: May 21, 2002

(54) ULTRASONIC MICROSCOPE FOR IMAGING THE INTERNAL REGIONS OF A SAMPLE BODY

(76) Inventors: Walter Arnold, Fliederstrasse 40, D-66119, Saarbrucken (DE); Andrzej Kulik, 18, Maladiere, CH-1022, Chavannes (CH)

( * ) Notice: Subject to any disclaimer, the term of this patent is extended or adjusted under 35 U.S.C. 154(b) by 0 days.

(21) Appl. No.: 09/462,607
(22) PCT Filed: Jun. 26, 1998
(86) PCT No.: PCT/DE98/01825
 § 371 Date: Mar. 27, 2000
 § 102(e) Date: Mar. 27, 2000
(87) PCT Pub. No.: WO99/02948
 PCT Pub. Date: Jan. 21, 1999

(30) Foreign Application Priority Data

Jul. 9, 1997 (DE) ............................................ 197 29 280

(51) Int. Cl.[7] .............................. G01H 3/12; G01B 5/28
(52) U.S. Cl. ........................................... 73/105; 73/606
(58) Field of Search ................................... 73/105, 606

(56) References Cited

U.S. PATENT DOCUMENTS 4,030,342 A  *  6/1977  Bond et al. ..................... 73/606
5,319,977 A  *  6/1994  Quate et al. .................... 73/606
5,675,075 A     10/1997 Arnold et al. ................. 73/105
5,852,233 A     12/1998 Arnold et al. ................. 73/105

OTHER PUBLICATIONS

Monchalin, J. "Optical Detection of Ultrasound", IEEE Transactions on Ultrasonics, Ferroelectrics, and Frequency Control, vol. UFFC–33, No. 5, Sep. 1986, pp. 485–499.*
Moreau, A. et al., "Detection of Ultrasound Using a Tunneling Microscope", J. Appl. Phys., vol. 72, No. 3, Aug. 1, 1992, pp. 861–864.*

* cited by examiner

Primary Examiner—Daniel S. Larkin
(74) Attorney, Agent, or Firm—Baker & Daniels

(57) ABSTRACT

An ultrasonic microscope for acquiring data from internal regions of a sample body is provided. The ultrasonic microscope includes an ultrasonic transmitter for providing a point source of ultrasonic waves for input-coupling into a sample body at a point in proportion to the dimensions of the sample body. Ultrasonically-induced excursions of a receiving tip can be detected with atomic resolution by using an ultrasonic detector that measures with high sensitivity resolution. The ultrasonic transmitter and the ultrasonic detector may be positioned relative to one another such that the ultrasonic detector can adopt several receiving positions for each transmitting position of the ultrasonic transmitter. A measurement data signal from the ultrasonic detector is stored and processed in a central processor. An image generator within the central processor uses a tomographic algorithm to reconstruct an image of at least one area inside the sample body from the measurement data.

9 Claims, 5 Drawing Sheets

FIG._3

ULTRASONIC MICROSCOPE FOR IMAGING THE INTERNAL REGIONS OF A SAMPLE BODY

BACKGROUND OF THE INVENTION

1. Field of the Invention

The invention concerns an ultrasonic microscope including an ultrasonic transmitter by means of which ultrasonic waves can be input-coupled in a sample body, an ultrasonic detector disposed on the opposite side of the sample body from the ultrasonic transmitter and by means of which the ultrasonic waves coupled into the sample body can be detected and which can be positioned relative to the sample body, and a central processor by means of which, as the ultrasonic detector assumes a series of positions relative to the sample body, measurement data assigned to the amplitudes of the input-coupled ultrasonic waves and the amplitudes of the ultrasonic waves detected by the ultrasonic detector can be stored and processed.

2. Description of the Related Art

U.S. Pat. No. 5,675,075 teaches an ultrasonic microscope, including an ultrasonic transmitter by means of which an entire sample body can be irradiated with ultrasonic waves. The prior device also includes an ultrasonic detector which measures with local resolution and which is realized in the form of an atomic force microscope, and by means of which ultrasound-induced deformations occurring on a detecting surface of the sample body can be detected via excursions of a receiving tip of the force microscope. Elasticity properties of the sample body can thus be measured with very high local resolution. The known device has the disadvantage, however, that only measurement values averaged over the region of passage of the ultrasonic waves can be acquired.

SUMMARY OF THE INVENTION

The present invention provides an ultrasonic microscope by which data can be acquired even over spatially limited areas in the interior of the sample body.

This task is accomplished by means of an ultrasonic microscope in which ultrasonic waves can be coupled into the sample body by the ultrasonic transmitter in a dotwise or point-sized manner compared to the dimensions of the sample body, in that the ultrasonic transmitter and the ultrasonic detector can be positioned mutually independently on the sample body, and in that a reconstructing unit or image generator is provided by means of which at least one image of internal regions of the sample body can be generated from the ultrasonic amplitudes transmitted by the ultrasonic transmitter at a plurality of transmitting positions and detected by the ultrasonic detector at a plurality of receiving positions with respect to each transmitting positions The fact that ultrasonic waves can be coupled into the sample body by the ultrasonic transmitter in a point-sized manner and that the ultrasonic transmitter and the ultrasonic detector can be positioned independently in relation to each other, the ultrasonic detector being able to detect ultrasonic amplitudes at a plurality of receiving positions for each transmitting position of the ultrasonic transmitter, makes it possible to obtain measurement data by means of which internal regions of the sample body can be imaged sharply by the reconstructing unit, for example on the basis of known tomographic image-generating techniques.

In a preferred embodiment, the ultrasonic detector comprises a force microscope whose resolution is preferably in the atomic range, down to a few tens of nanometers; in a further embodiment, the ultrasonic detector is provided with a tunnel microscope whose resolution is preferably in the atomic range down to a few tens of nanometers.

When a force microscope is used, it is advantageous to provide an optically or capacitively functioning detection unit to detect the excursions of a receiving tip of the force microscope.

In various embodiments, the ultrasonic transmitter is a focusing ultrasonic lens coupled to an ultrasonic transducer, a force microscope coupled to an ultrasonic transducer, or an optical unit comprising an exciting light source, a modulator, and a focusing optic and serving to generate ultrasonic waves on the basis of the thermoelastic effect.

To produce a three-dimensional image of the sample body, it is provided to position the ultrasonic transmitter over the coupling-side surface of the sample body at a plurality of transmitting positions in a grid corresponding to the local resolving power of the ultrasonic transmitter, and, for each transmitting position of the ultrasonic transmitter, to position the ultrasonic detector, also in a grid corresponding to its local resolving power, at a plurality of receiving positions on a detecting surface opposite the coupling-side surface, over a detection-side surface of the sample body in a region where the ultrasound-induced deformation of the detecting surface can be detected. In this manner, data can be acquired from which a complete three-dimensional image of the sample body or images of any desired slices can be reconstructed.

It is also advantageous to provide a sample-body displacing device by means of which the sample body can be displaced in relation to the ultrasonic transmitter to permit irradiation at additional transmitting positions.

BRIEF DESCRIPTION OF THE DRAWINGS

Further advantageous embodiments of the invention will become more apparent and the invention itself will be better understood by reference to the following description of exemplary embodiments provided with reference to the following drawings wherein.

Corresponding reference characters indicate corresponding parts throughout the several views. The exemplification set out herein illustrates one preferred embodiment of the invention, in one form, and such exemplification is not to be construed as limiting the scope of the invention in any manner.

DETAILED DESCRIPTION OF THE INVENTION

Figure 1:
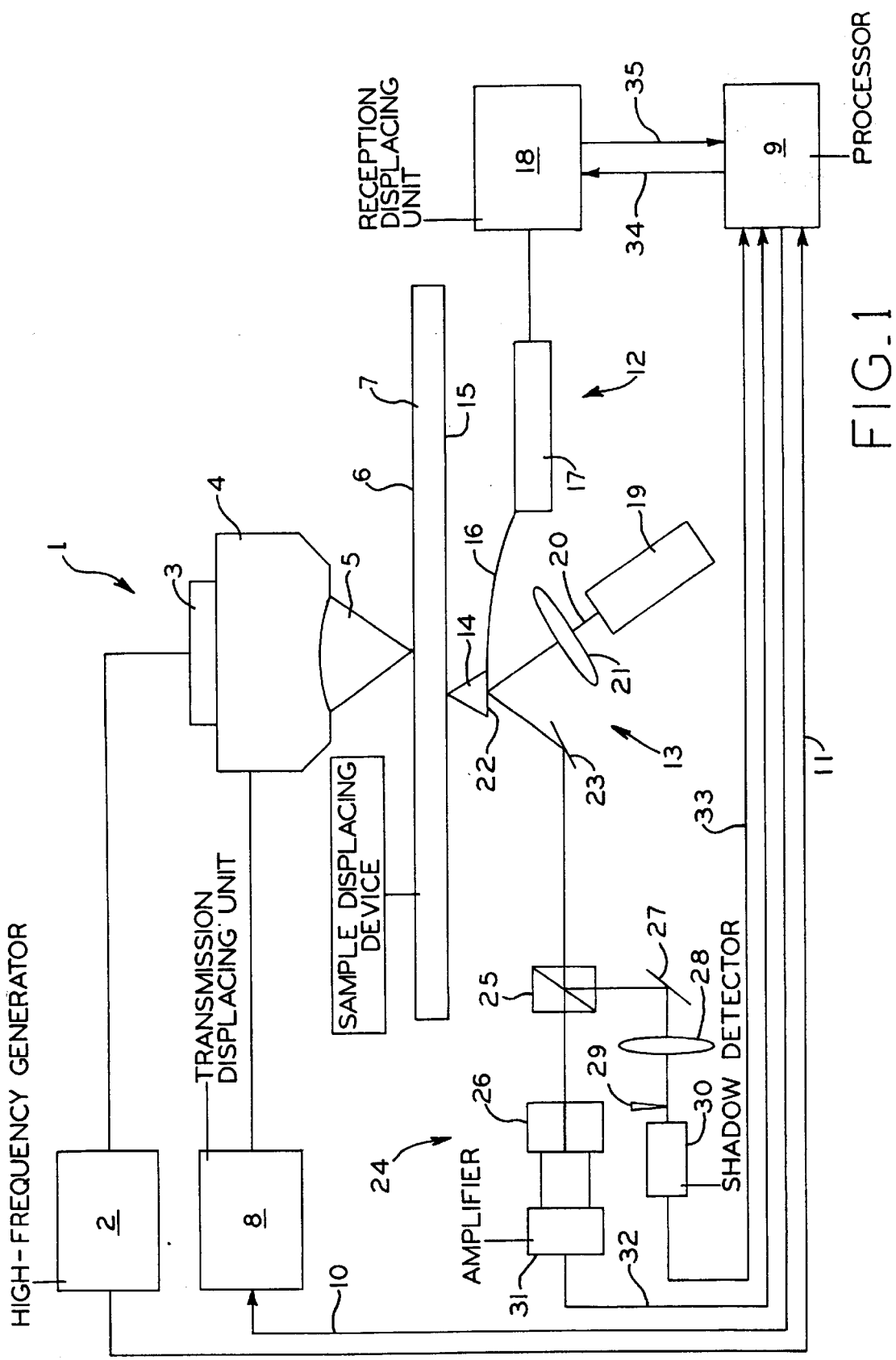
FIG. 1 is a block circuit diagram of an exemplary embodiment of an ultrasonic microscope with an ultrasonic lens for point-sized input coupling of ultrasonic waves.

FIG. 1 is a block circuit diagram of an exemplary embodiment of an ultrasonic microscope. The ultrasonic microscope according to FIG. 1 is provided with an ultrasonic transmitter 1, comprising an ultrasonic transducer 3 connected to a high-frequency generator 2. Said ultrasonic transducer 3 is coupled to an ultrasonic lens 4, by means of which an ultrasonic beam 5 can be focused on a input-coupling surface 6 of a sample body 7. The diameter of the focal spot of the ultrasonic lens 4 is typically in the range of a few micrometers to a few tens of micrometers and is therefore dot-sized or point-sized in comparison to the size of typical macroscopic sample bodies 7 so that the electronic beam appears to have been generated by a point source. Both the ultrasonic transducer 3 and the ultrasonic lens 4 are connected mechanically to a transmission displacing unit 8, by means of which an emitted ultrasonic beam 5 can be positioned at a number of transmitting positions on the input-coupling surface 6.

The ultrasonic microscope according to FIG. 1 is provided with a central processing unit or processor 9, by means of which transmission displacing unit 8 can be driven via a transmission positioning line 10 to effect defined positioning of the ultrasonic beam 5. Ultrasonic amplitude values corresponding to the amplitude of ultrasonic beam 5 can be stored as measurement data in central processing unit 9 via a transmission amplitude line 11.

The ultrasonic microscope according to FIG. 1 further comprises a receiving force microscope 12 forming part of an ultrasonic detector 13 and preferably operating in the near field, i.e., in a substantially aperture-limited manner. Receiving force microscope 12 is provided with a receiving tip 14, which, with a local resolution preferably in the range of typically no more than a few tens of nanometers, especially preferably with atomic resolution, can be positioned at a distance from a detecting surface 15 opposite the input-coupling surface 6 of the sample body 7 such that at said distance the magnitude of the wavelength of the input-coupled ultrasonic waves has no significant effect on the intensity distribution at the detecting surface 15, preferably in the near field of the ultrasonic waves emanating from the point-sized input coupling region. Receiving tip 14 is fastened at one end to a receiving spring 16, realized, for example, as a leaf spring, the other end of which is disposed on a receiving-spring mounting 17. Receiving-spring mounting 17 is connected mechanically to a reception displacing unit 18 by means of which receiving tip 14 can be positioned at a plurality of receiving positions over detecting surface 15 for each transmitting position.

The ultrasonic detector 13 according to FIG. 1 is further provided with a scanning light source 19, realized, for example, as a lager, whose emitted scanning beam 20 can be focused via a scanning focusing optic 21 on an at least partially reflective scanning face 22 of receiving tip 14 or receiving spring 16. The portion of scanning beam 20 reflected by scanning face 22 can be guided to an optical detection unit 24 via a scanning deflection unit 23. Optical detection unit 24 is provided with a beam splitter 25, by means of which the portion of scanning beam 20 incident on optical detection unit 24 can be guided to a segment detector 26 and, via a deflector unit 27 and a focusing detection optic 28 and passing through a partial-shadow-forming element 29 disposed in the focal region of detection optic 28, to a shadow detector 30.

Segment detector 26, which is constructed of two adjacent detecting surfaces, has a comparatively small bandwidth that is smaller than the frequency of the ultrasonic waves coupled into sample body 7. The outputs of segment detector 26, each of which is assigned to a detecting surface, are connected to a normalizing amplifier 31, which normalizes the difference between the photoelectric voltages of the detecting surfaces of segment detector 26 to their cumulative value and amplifies said value. Segment detector 26 thus serves to detect low-frequency deflections of receiving tip 14 that are caused in particular by the topography of detecting surface 15 and are slower than ultrasound-induced high-frequency excursions of the receiving tip 14.

Shadow detector 30, which is provided with only one detecting surface, has a bandwidth that corresponds at least to the frequency of the ultrasonic waves 5 coupled into sample body 7. Shadow detector 30 serves to detect the ultrasound-induced high-frequency excursions of receiving tip 14, which condense into an alternating partial intensity of scanning beam 20 that is induced by partial-shadow-forming element 29 and is incident on shadow detector 30.

Central processor 9 is able to store the output signals from normalizing amplifier 31 via a low-frequency-signal line 32 and the output signals from shadow detector 30 via a high-frequency-signal line 33. Furthermore, reception displacing unit 18 can be driven by central processing unit 9 via a drive line 34, in which case receiving-position signals assigned to the receiving position of receiving tip 14 can be transmitted via a receiving-position line 35 from reception displacing unit 18 to central processing unit 9.

With the ultrasonic microscope according to FIG. 1, ultrasonic beam 5 and receiving tip 14 can preferably be positioned relative to each other when sample body 7 is at rest. In a preferred measurement technique, at each position of ultrasonic beam 5, receiving tip 14 is positioned at least over the region of detecting surface 15 in which an ultrasound-induced high-frequency excursion of receiving tip 14 can be detected. The output signals from high-frequency generator 2 corresponding to the input-coupled ultrasonic amplitudes, on the one hand, and the intensity signals from shadow detector 30 and normalizing amplifier 31 corresponding to the amplitudes of the deflections and to the high-frequency excursions, on the other hand, can be stored as measurement data by central processing unit 9 as a function of each transmitting position of ultrasonic beam 5 and the receiving positions of receiving tip 14 that are assigned to said transmitting position.

Figure 2:
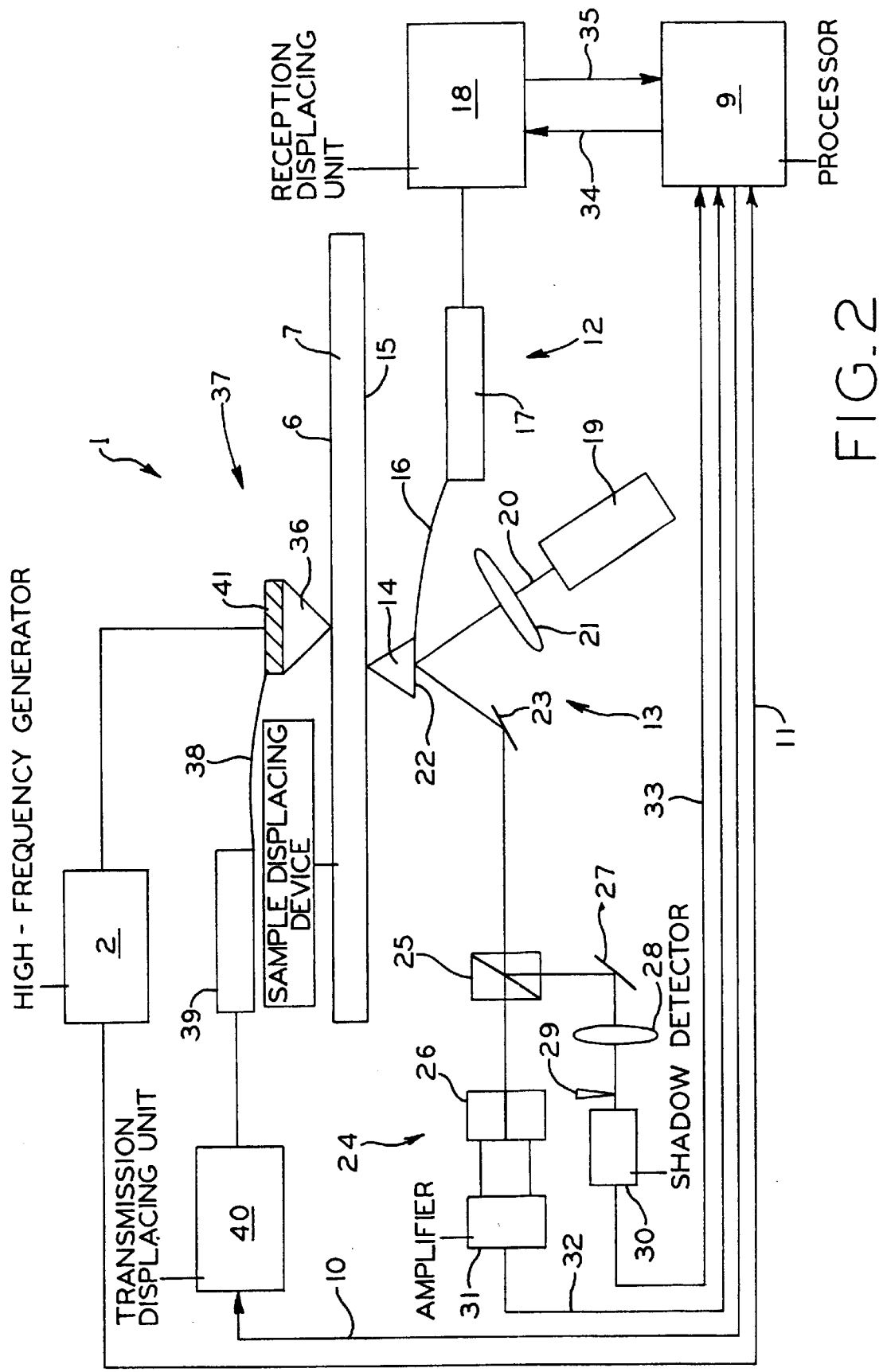
FIG. 2 is a block circuit diagram of a further exemplary embodiment of an ultrasonic microscope with a force atomic microscope for point-sized input coupling of ultrasonic waves.

FIG. 2 is a block circuit diagram of a further exemplary embodiment of an ultrasonic microscope, which, as a modification with respect to the exemplary ultrasonic microscope of FIG. 1, effects the coupling of ultrasonic waves into sample body 7 by the use of a force transmitting microscope 37 comprising a transmitting tip 36 and possessing a high local resolving power of, typically, a few tens of nanometers. Said transmitting tip 36 is mounted at one end on a transmission spring 38 realized as a leaf spring, whose other end is fastened to a transmission-spring mounting 39. Transmission-spring mounting 39 is connected mechanically to a transmission displacing unit 40, by means of which transmitting tip 36 can be positioned over the input-coupling surface 6 of sample body 7. Mounted on transmitting tip 36 is an ultrasonic transducer 41, preferably realized as a piezoelectric device, which is connected to the high-frequency generator 2 of the ultrasonic transmitter 1. When ultrasonic transducer 41 is impacted on by a high frequency that can be generated by means of high-frequency generator 2, ultrasonic waves that are point-sized in comparison to the dimensions of sample body 7 can be coupled into sample body 7 via transmitting tip 36.

Figure 3:
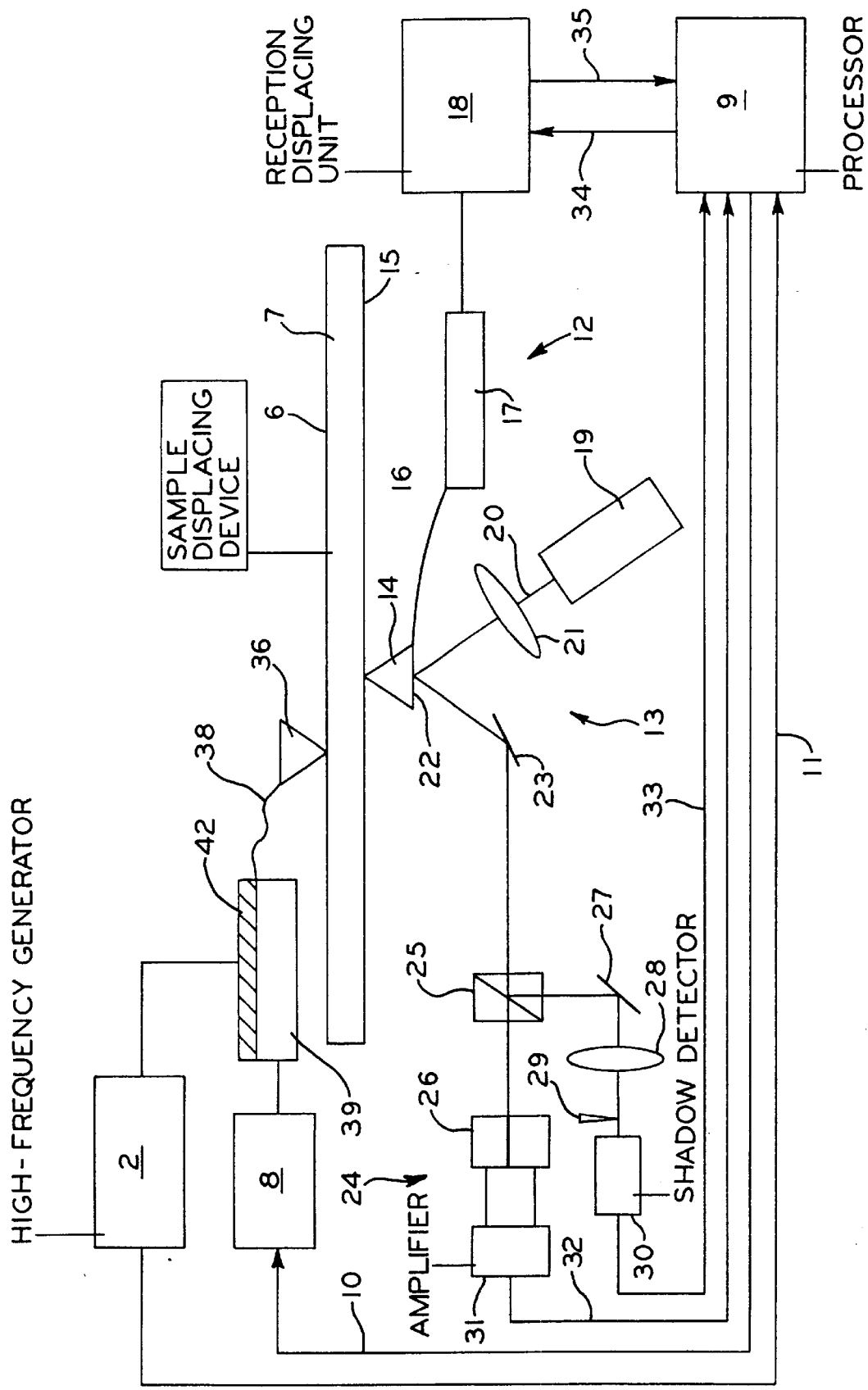
FIG. 3 is a block circuit diagram of a further exemplary embodiment of an ultrasonic microscope with a force microscope modified with respect to the exemplary embodiment of FIG. 2.

FIG. 3 shows a further exemplary embodiment of an ultrasonic microscope, in which, as a modification with respect to the exemplary embodiment of FIG. 2, an ultrasonic transducer 42 is coupled to the transmission-spring mounting 39. When transmission-spring mounting 39 is impacted by ultrasonic waves generated by the high-frequency generator 2 connected to ultrasonic transducer 42 and by ultrasonic transducer 42, transmission spring 38 is set in high-frequency vibration, so that transmitting tip 36 acts as a point source and induces ultrasonic waves dotwise or pointwise in sample body 7.

Figure 4:
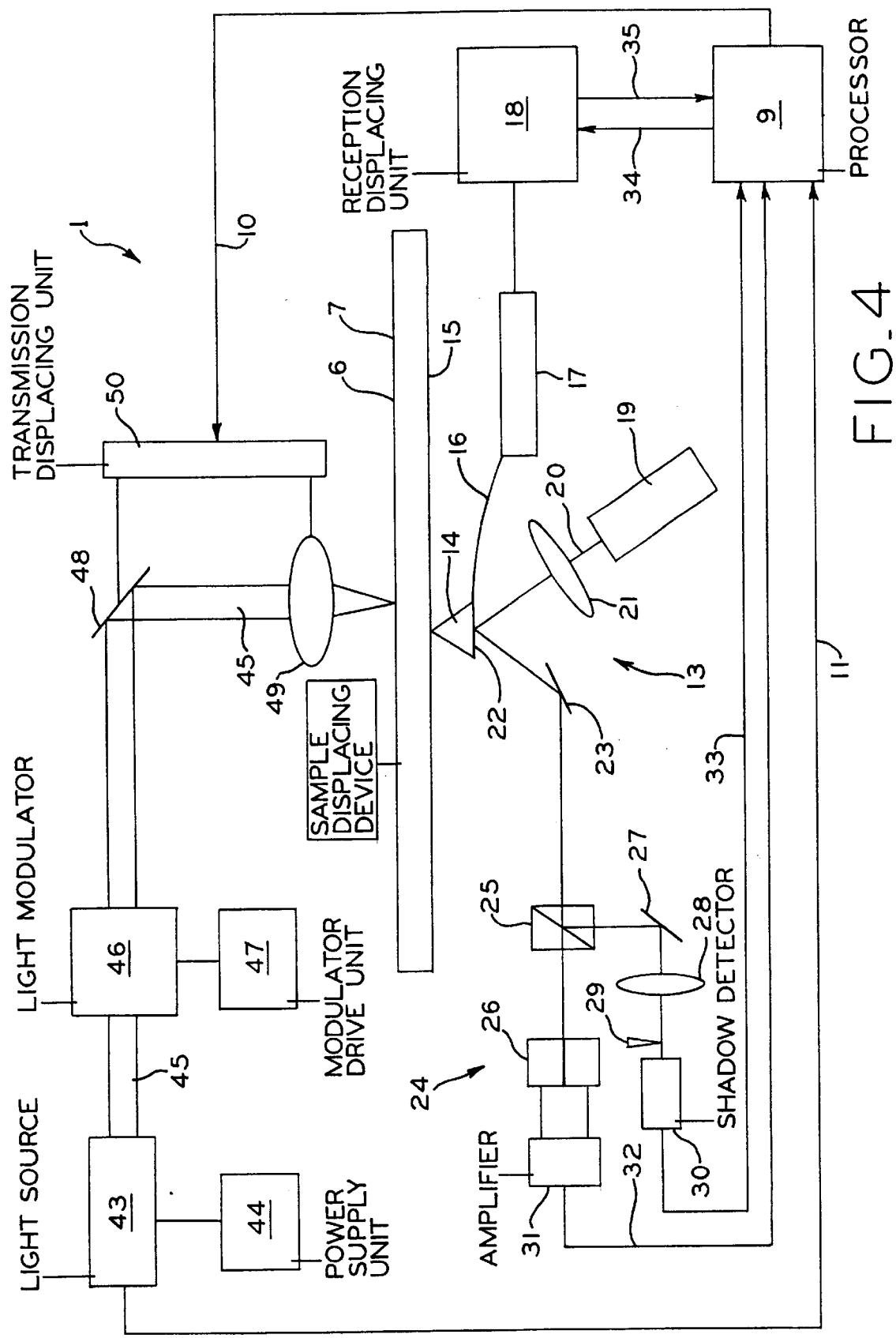
FIG. 4 is a block circuit diagram of a further exemplary embodiment of an ultrasonic microscope with an optical arrangement for point-sized generation of ultrasonic waves.

FIG. 4 shows a further exemplary embodiment of an ultrasonic microscope; the components corresponding to the exemplar embodiments of FIGS. 1 to 3 are provided with the same reference numerals and are not described below in further detail. The ultrasonic transmitter 1 in the ultrasonic microscope of FIG. 4 is provided with an exciting light source 43, preferably realized as a laser, which can be driven by a power supply unit 44 to emit an exciting light beam 45 which is substantially parallel in the exemplary embodiment of FIG. 4. Disposed after the exciting light source 43 is an exciting light modulator 46, by which the intensity of an exciting light beam 45 incident thereon can be high-frequency-modulated under the control of a modulator drive unit 47.

The ultrasonic transmitter 1 according to FIG. 4 is further provided with an exciting-light deflecting optic 48 and a diffraction-limited exciting-light focusing optic 49, by means of which the intensity-modulated exciting light 45 can be focused on the coupling surface 6 of sample body 7, it being possible on the principle of the thermoelastic effect to generate ultrasonic waves as a point source in a very small region compared to the dimensions of the sample body 7.

Exciting-light deflecting optic 48 and exciting-light focusing optic 49 are connected mechanically to a transmission displacing unit 50, by means of which the focal region of the exciting light beam 45 can be guided over coupling surface 6 of sample body 7. Transmission displacing unit 50 is connected to central processing unit 9 for purposes of control.

Figure 5:
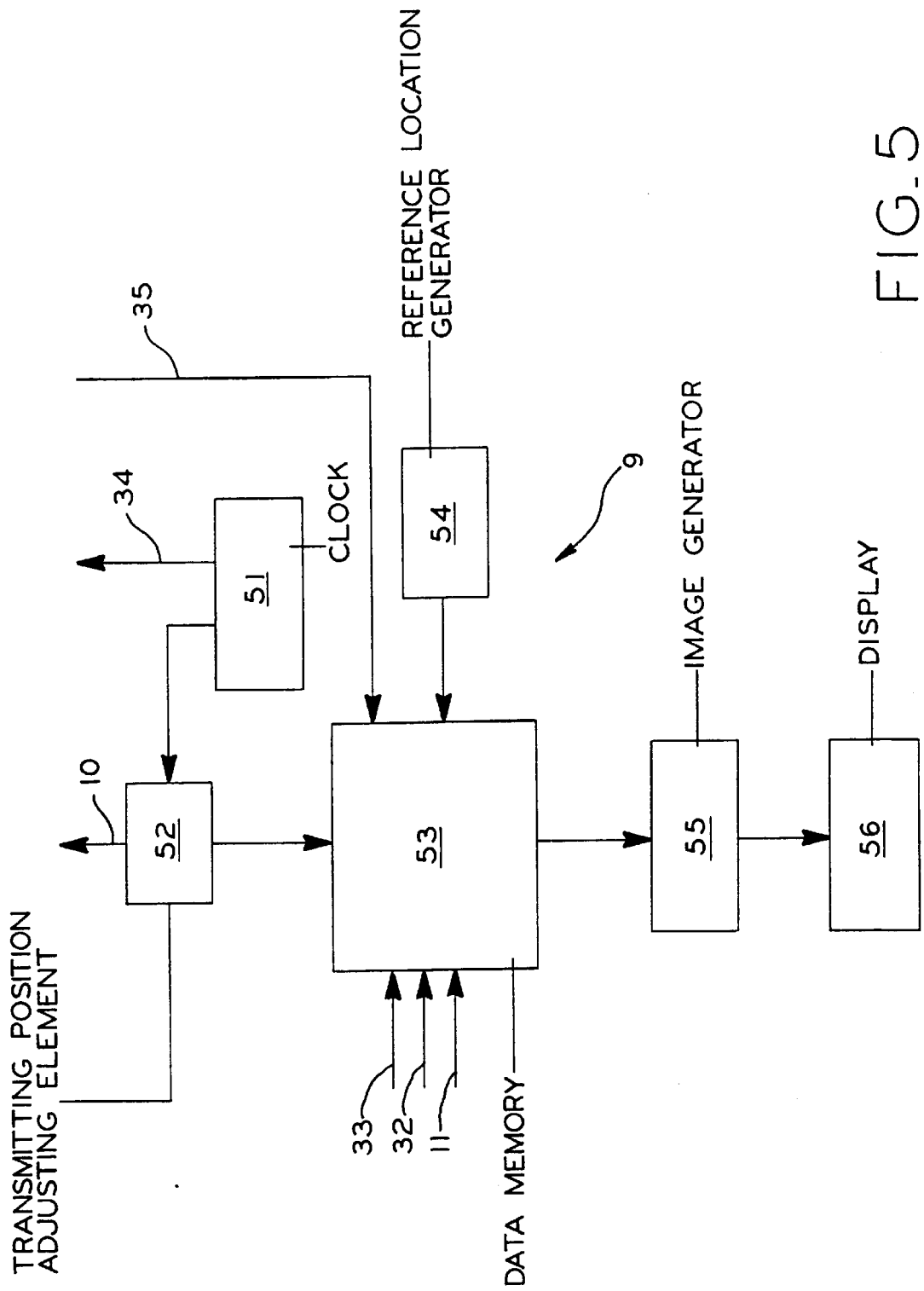
FIG. 5 is a block circuit diagram of an exemplary embodiment of a central processing unit of an ultrasonic microscope.

FIG. 5 is a block circuit diagram of an exemplary embodiment of the central processing unit or processor 9 according to the ultrasonic microscope described in exemplary fashion with reference to FIGS. 1 to 4. Central processing unit 9 is provided with a clock 51 to which is connected a transmitting-position adjusting element 52. By means of transmitting-position adjusting element 52, ultrasonic beam 5, transmitting tip 36, and the focal region of exciting light beam 45 can respectively be positioned in a set manner in a plurality of transmitting positions with respect to coupling surface 6 when the respective transmission displacing unit 8, 40, 50 is acted upon by suitable control signals via transmitting-position line 10. Further, clock 51 is connected to reception displacing unit 18 via control line 34, so that at each transmitting position of ultrasonic beam 5, transmitting tip 36 or focused exciting light beam 45, respectively, receiving tip 14 is positioned at a plurality of receiving positions for detecting the ultrasound-induced high-frequency excursions and the topographically induced low-frequency deflections at detecting surface 15 opposite coupling surface 6.

Transmitting-position signals delivered by transmitting-position adjusting unit 52 and assigned to the position of ultrasonic beam 5, transmitting tip 36, and the focal region of focused exciting light beam 45, as well as detection-position signals delivered by the reception displacing unit 18 and assigned to the receiving position of receiving tip 14, can be sent to a data memory 53 for storage together with the amplitudes of the amplitude signals assigned to the input-coupled ultrasonic waves and present on transmission-amplitude line 11, as well as the intensity signals present on low-frequency line 32 and high-frequency line 33. A reference location signal from a reference location generator 54 can also be stored in data memory 53 and serves as a reference signal for making the conversion into absolute spatial coordinates.

After the termination of a measurement cycle, including the relative positioning of receiving tip 14 with respect to the ultrasonic lens 4 generating the ultrasonic waves, the transmitting tip 36, and the exciting-light focusing optic 49 focusing the exciting light beam 45, a reconstructing unit or image generator 55 disposed after data memory 53 can be used to combine the measurement data on the basis of image-generating tomographic algorithms to form a locally resolved intensity image of at least one internal layer of sample body 7.

The tomographic algorithm can be made in each case to take advantage of the fact that the attenuation of the ultrasonic waves coupled into sample body 7 at input-coupling surface 6 can be detected substantially at each relative position by receiving tip 14 operating in the near field, and given the displacement of the ultrasonic beam 5, the transmitting tip 36, and the focal region of the exciting light beam 45 and the repeated positioning of transmitting tip 14 at each of these transmitting positions, by appropriate combination of the location data and intensity data stored in data memory 53 at least one predetermined layer can be reconstructed with a sharpness that corresponds to a total resolving power determined by the size of the point-sized coupling region and the local resolving power of ultrasonic detector 13. If a large number of layers is reconstructed with a precision that does not exceed the total resolving power, it is even possible to reconstruct a three-dimensional image of the internal structure of the sample body 7.

In the exemplary embodiments depicted in FIGS. 6–9, the ultrasonic detector is comprised of tunnel microscope unit 57. Tunnel microscope unit 57 is comprise of tunnel microscope 59 and suspension unit 58.

In the exemplary embodiments depicted in FIG. 5, the data processed by means of reconstructing unit or image generator 55 can be output in an output unit or display 56 as tomograms or three-dimensional representations.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An ultrasonic microscope for the examination of a sample body, said ultrasonic microscope comprising:
an ultrasonic transmitter disposed on a coupling side surface of a said sample body, said ultrasonic transmitter displaceable to a plurality of transmitting positions relative to a said sample body, said ultrasonic transmitter providing a point source of input-coupled ultrasonic waves to a said sample body in proportion to the dimensions of a said sample body;
an ultrasonic detector disposed on a detection side surface of a said sample body opposite said coupling side surface, said ultrasonic detector independently positionable for each said transmitting position to a plurality of receiving positions for receiving said ultrasonic waves from said ultrasonic transmitter, said ultrasonic detector measuring the amplitude of said ultrasonic waves and forming amplitude data signals therefrom at each of said receiving positions for each transmitting position of the plurality of transmitting positions and location data representative of the positions of the ultrasonic transmitter and the ultrasonic receiver;

a central processor for processing said amplitude data signals as a function of each transmitting position and the plurality of receiving positions allocated to said transmitting position and generating data signals therefrom and storing said data signals; and an image generator for generating a three dimensional image of an internal region of a said sample body by combining said stored data signals and said amplitude data signals.

2. The ultrasonic microscope of claim 1, wherein said ultrasonic detector comprises a tunnel microscope, said tunnel microscope capable of atomic resolution.

3. The ultrasonic microscope of claim 1, wherein said ultrasonic detector comprises a force atomic microscope having a receiving tip, said force atomic microscope capable of atomic resolution.

4. The ultrasonic microscope of claim 3, wherein said ultrasonic microscope includes an optical detection unit for detecting the excursions of said receiving tip.

5. The ultrasonic microscope of claim 1, wherein said ultrasonic transmitter comprises an ultrasonic transducer having a focusing ultrasonic lens.

6. The ultrasonic microscope of claim 1, wherein said ultrasonic transmitter.

7. The ultrasonic microscope of claim 1, wherein said ultrasonic transmitter comprises a light source, a modulator, and a focusing optic, said ultrasonic transmitter focusing an intensity-modulated light beam on a said sample body.

8. The ultrasonic microscope of claim 1, wherein said image generator employs a tomographic algorithm to generate said image from said data signal.

9. The ultrasonic microscope of claim 1, including a sample body displacing device for displacing a said sample body relative to said ultrasonic transmitter.

* * * * *

UNITED STATES PATENT AND TRADEMARK OFFICE
CERTIFICATE OF CORRECTION

PATENT NO. : 6,389,885 B1
DATED : May 21, 2002
INVENTOR(S) : Walter Arnold et al.

It is certified that error appears in the above-identified patent and that said Letters Patent is hereby corrected as shown below:

Column 8,
Line 11, after the word "transmitter" please add -- comprises a force microscop coupled to an ultrasonic transducer. --

Signed and Sealed this

Eighth Day of October, 2002

Attest:

Attesting Officer

JAMES E. ROGAN
Director of the United States Patent and Trademark Office